United States Patent [19]

Honzawa

[11] Patent Number: 5,286,848

[45] Date of Patent: Feb. 15, 1994

[54] LANTHANIDE CRYPTATE OF TRISPHENANTHROLINE

[75] Inventor: Katsu Honzawa, Hamamatsu, Japan

[73] Assignee: Hamamatsu Photonics K.K., Hamamatsu, Japan

[21] Appl. No.: 51,819

[22] Filed: Apr. 26, 1993

Related U.S. Application Data

[63] Continuation of Ser. No. 519,594, May 7, 1990, abandoned.

[51] Int. Cl.$^5$ .................... C07K 3/08; C07K 13/00
[52] U.S. Cl. .................... 530/363; 530/400; 530/402; 530/830; 534/15
[58] Field of Search ............ 530/363, 400, 402, 830; 534/15

[56] References Cited

U.S. PATENT DOCUMENTS

| | | | |
|---|---|---|---|
| 4,257,955 | 3/1981 | Gansow et al. | 534/15 |
| 4,772,563 | 9/1988 | Evangelista et al. | 534/15 |
| 4,837,169 | 6/1989 | Toner | 534/15 |

OTHER PUBLICATIONS

Rudinger, Peptide Hormones, Parson (ed.), U Park Press, Baltimore, pp. 1-7 (1976).
Rodriguez-Ubis et al., Helvetica Chimica Acta-vol. 67, pp. 2264-2269 (1984).
Agnew. Chem. Int. Ed. Engl. 26 (1987) No. 12, pp. 1266-1267.

*Primary Examiner*—Christina Y. Chan
*Attorney, Agent, or Firm*—Cushman, Darby & Cushman

[57] ABSTRACT

A photoactive lanthanide complex of 2,2′,2″,9,9′,9″-bis[nitrilotri(methylene)]tris(1,10-phenanthroline) and its functional derivative capable of bonding with substrate such as polymer and protein are provided. The lanthanide complex is usable for photosynthesis and photoimmunoassay.

2 Claims, 2 Drawing Sheets

LANTHANIDE CRYPTATE OF TRISPHENANTHROLINE

This is a continuation of application Ser. No. 07/519,594, filed on May 7, 1990, which was abandoned upon the filing hereof.

BACKGROUND OF THE INVENTION

The present invention relates to a novel lanthanide chelate compound, and more particularly a lanthanide complex of phenanthroline cryptand in which lanthanide ion is occluded in the cavity of the cryptand. The compound is stable and photo active and usable for immunoassay or photosynthesis when it is combined with a variety of substrates.

Hitherto, a coordination compound of lanthanide ion such as europium and terbium ions has been reported, as a desirable photoimmunoassay labelling agent due to its emission sharpness and ability of delayed time performance. For example, Ilkka Hemmila et al, Analytical Biochemistry, Vol. 137, pp 335-343 (1984) disclose chelate compounds of Eu with a variety of beta-diketones, L. M. Vallarino et al, "Automation Cancer Cytology and Cell Image Analysis" pp 31-45 (1979) edited by N. J. Pressman, disclose octa-coordinate Eu(III) compound containing three beta-ketonato ligands and one ortho-phenanthroline ligand. Further, Juan-carlos Rodrigez-Ubis et al, Helv. Chim. Acta, Vol. 67 pp 2264-2269, report an NaBr complex of a cryptand, 2,2',2'',9,9',9''-bis[nitrilotri(methylene)]tris(1,10-phenanthroline) of the formula,

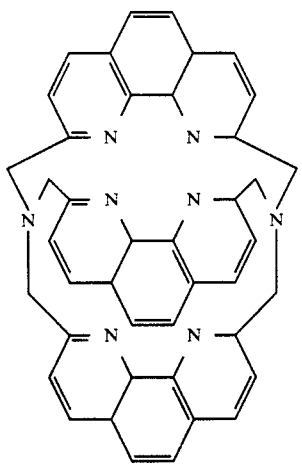

An object of the present invention is to provide a novel lanthanide complex of the cryptand of the formula (I') described below.

Another object of the present invention is to provide a new photoactive material labelled with the lanthanide complex of the cryptand of the formula (I') described below.

SUMMARY OF THE INVENTION

According to the present invention, there is provided a lanthanide complex of 2,2',2'',9,9',9''-bis[nitrilotri(methylene)]tris(1,10-phenanthroline), of the following formula, designated formula (I'), which complex may otherwise be referred simply to as "cryptate" herein,

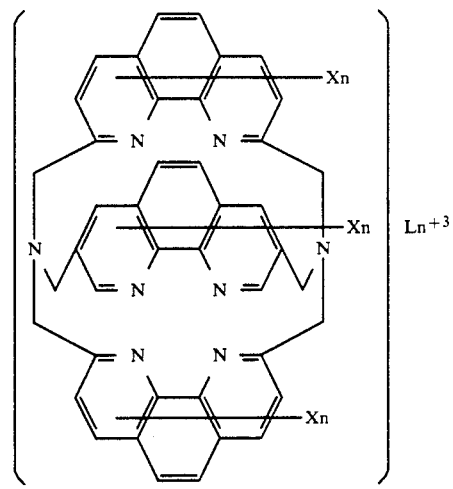

wherein X denotes a hydrogen atom or a phenyl group and the total number of "n" is at least 1 and each "n" is 0, 1 or 2 when X is a phenyl group.

DESCRIPTION OF THE PREFERRED EMBODIMENT

Figure 1:
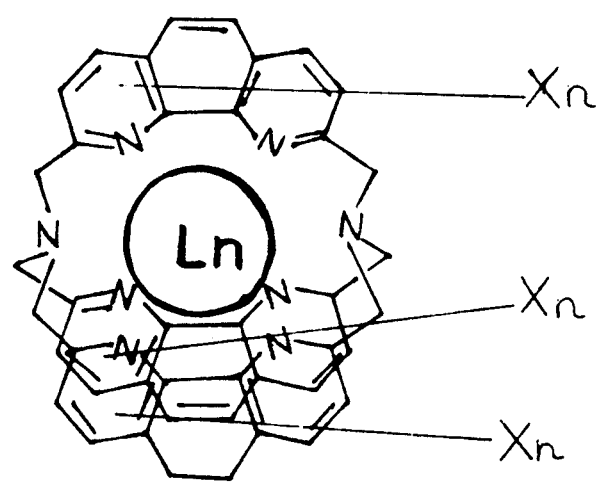
FIG. 1 shows a schematic, steric view of the principal cryptate of the present invention.

The cryptate of the present invention has a steric structure shown in the FIG. 1 where lanthanide ion is occluded in the cavity of the cryptand of three phenanthroline (i.e. 2,2',2'',9,9',9''-bis[nitrilotri(methylene)]-tris(1,10-phenanthroline), which cryptand is referred simply to mere "cryptand", and is extremely stable.

Figure 2A:
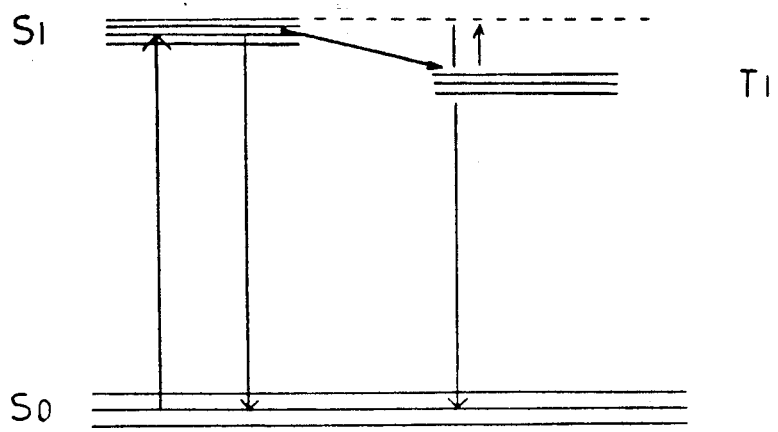
FIG. 2A shows an explanatory view of energy level transition of lanthanide ion.
Figure 2B:
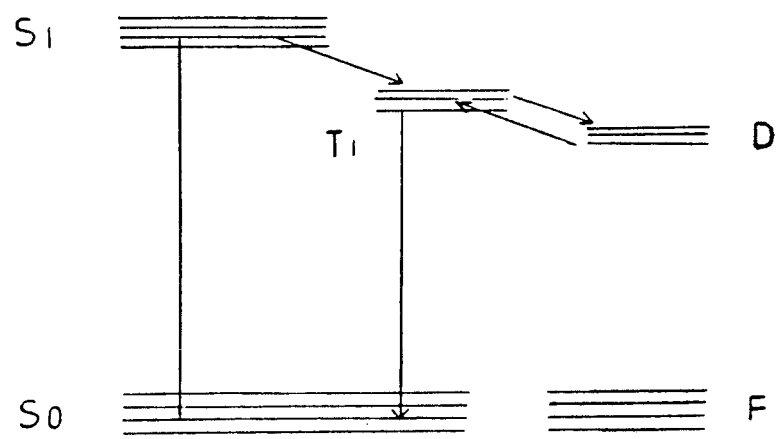
FIG. 2B shows an explanatory view of energy level transition of cryptate.

As shown in FIG. 2A, a lanthanide ion itself, in general, when exposed by light energy, the initial energy level (S) increases to level (S) and then decreases to the triplet energy level (T) to effect emission, and thus is evaluated as delayed time fluorescenser. On the other hand, as shown in FIG. 2B, in the present cryptate the increased level (S) decreases to lanthanide energy level (D) via (T) and then effects emission, wherein the energy level (F) is the ground state of lanthanide ion.

The lanthanide ion used in the present invention is any one, though europium, terbium, samarium and dyspridium are desirable in this order due to their emission ability.

The cryptate shown by the FIG. 1 solves the problems seen in the conventional coordination compounds, that is, ease of the release of metal atom from the ligand, the tendency of putting out of the fluorescence emission and the low energy transition efficiency on the ligand.

The novel cryptate of the present invention can be easily prepared by slightly modifying the aforementioned method of Rodriguez et al which is incorporated by reference herein. Thus, the cryptand prepared according to the Rodriguez's method is allowed to react with a strong acid salt of lanthanides such as nitric acid salt. The cryptand and cryptate each having an aromatic ring group such as a phenyl group can also be obtained from the phenanthroline compound.

The cryptate derivative having the functional group can be prepared by introducing a functional group capable of bonding directly or indirectly to a —NH$_2$ group or —SH group at any position of the aromatic ring group contained in the cryptand. By the introduction the cryptate of the present invention can considerably enlarge its use, permitting covalently bonding with a substrate such as a high molecular weight substance having a —NH$_2$ or —SH group, for example, proteins, especially antibodies, a polymer and the like. The combined substance can be used in a fluorescent immunoassay or light modification.

The functional group is selected, for example, from halosulfonyl, haloacetamido, ethyleneiminosulfonyl, maleimido, isothiocyanato groups and the like which can be covalently bonded with amino or sulfhydryl group. An aromatic ring, especially a phenyl group, easily permits the introduction of the functional group. Thus, a cryptate containing a phenyl group substituent is preferable for the purpose.

Also, the functional group may be one capable of bonding to the substrate through a bifunctional compound. Thus, amino group is, for example, selected therefor. The example of the bi-functional compound for amino group is a water soluble carbodiimide such as 1-ethyl-3-(3-dimethylaminopropyl) carbodiimide, glutaraldehyde, or bis-diazotized benzidine. The bonding technique to the substrate is well known as a method of bonding a hapten such as polypeptide to a carrier protein for giving the hapten an antigenicity.

The functional group introduced is sufficient in an amount of 1 per mol of cryptate but may be more. The introduction of the functional group to an aromatic ring of a coordination compound or photoactive compound is well known. For example, C. F. Meares and T. Wensel (Acc. Chem. Res. 1984, 17, pp 202–209) disclose the reduction of (p-nitrobenzyl-ethylenediamine tetraacetic acid to (p-amino-benzyl) compound of which amino group is then converted to a isothiocyanato group by reacting with thiophosgen and to haloacetamido group by haloacetohalide, respectively. Also, J. K. Weltman et al (J. Biol. Chem., vol. 18, May 10 pp 3173–3177) report the preparation of N-(3-pyrene) maleimide by reacting 3-aminopyrene with maleic anhydride to form N-(3-pyrene) maleamic acid which is then cyclized under dehydration by reacting with acetic anhydride to form N-(3-pyrene) maleimide. Further, W. H. Scouten et al (Biochimica et Biophysica Acta, 336, 1977, pp 421–426) report the preparation of N-dansylaziridine by reacting dansyl chloride with ethylenimine in the presence of triethylamine. All of the references are incorporated by reference herein.

In the introduction of functional group, any method including the above methods may be used. However, it is noted that a phenyl group with which phenanthroline is substituted is more easily subjected to such introduction, and the use of phenanthroline compound having a phenyl substituent is desirable.

The introduction of functional group may be effected with respect to phenanthroline or phenylphenanthroline compound itself, cryptand or cryptate thereof. In general, phenanthroline compound or its cryptand would be subjected to such introduction. In case of the former, the number of the functional group would be optionally selectable.

The kind of functional group is suitably selected depending upon the kinds of bonding objective amino or sulfhydryl group in a substrate to be bonded. If the objective high molecular weight substance is an antibody, a halosulfonyl such as chlorosulfonyl group or isothiocyanate group is selected for IgG having an objective amino group in the side chain and a haloacetamide such as iodoacetamide, or ethyleneiminosulfonyl or maleimino group for Fab' having a sulfhydryl group. Also, an amino group is introduced if a bifunctional compound such as glutalaldehyde or others as mentioned above is used for the substrate having a free amino group.

Thus, the present invention provides a functional cryptate derivative of the formula

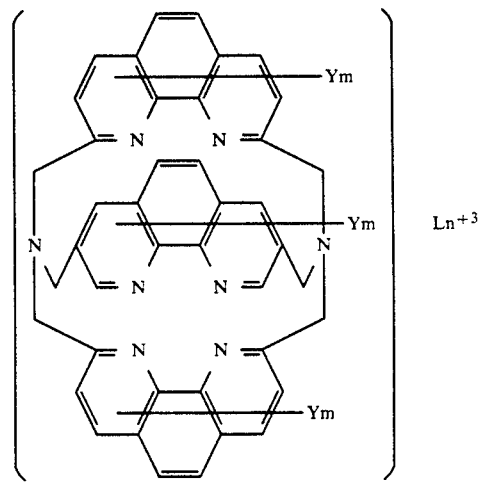

wherein Y is a functional group capable of directly or indirectly bonding to amino or sulfhydryl group, which may be amino, isothiocyanato, halosulfonyl, haloacetamido, maleimido, ethyleneiminosulfonyl group, or a phenyl group having the same, and the total number of "m" is at least 1 and each "m" is 0, 1 or 2.

An example of the preparation of the present cryptate and its functional derivative from the starting compound of 4,7-diphenyl-2,9-dimethyl-1,10-phenanthroline is shown by the following formula steps:

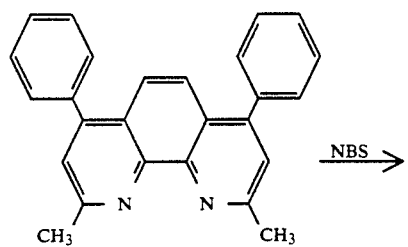

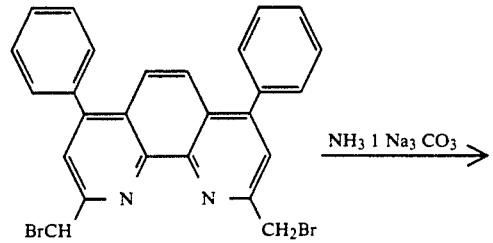

-continued

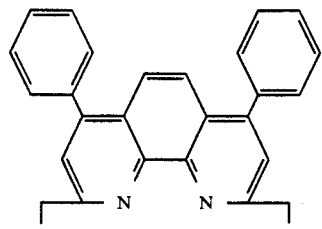
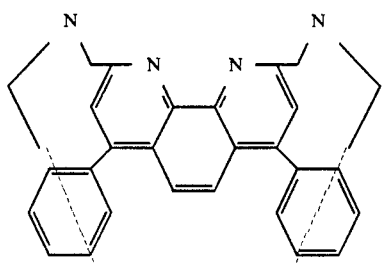
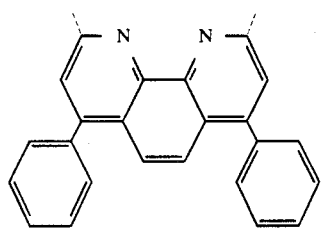

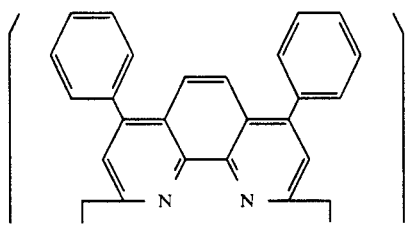
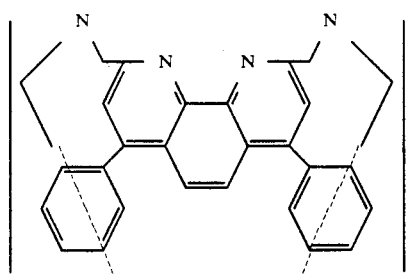 Eu+3 ClSO3H →
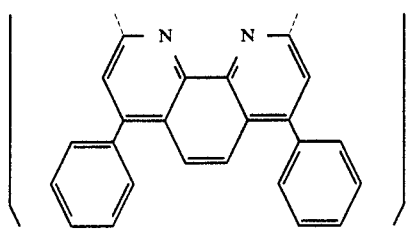

-continued

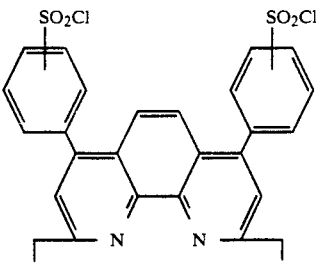
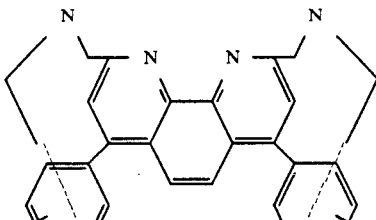
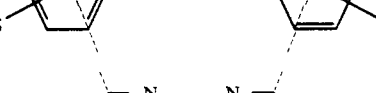 Eu+3
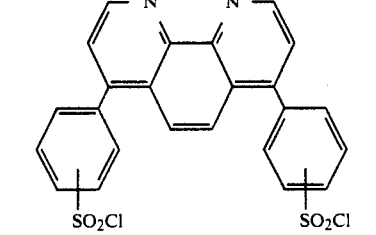

The present cryptate is soluble in water. The cryptate itself can be used as a wave length modifier in a form embedded in a polymer film, sheet or beads or photo synthesizer. The cryptate derivative having the functional group can be bonded with a variety of high molecular weight substances to form a permanent photoactive material. In particular, an antibody labelled with the present cryptate derivative is usable for delayed time performance fluorescent immunoassay. The labelled antibody is dissolved in water or immobilized on solid as carrier and may be used in immunoassay and affinity chromatography. Also, covalently labelled polymer is usable as a wave length modifying film for ultraviolet ray sensivity in silicon photodiode and CCD camera or as a light absorption film.

The invention is explained in detail by referring to the following Examples which should not be construed to limit the invention defined in the accompanying Claims.

EXAMPLE 1

15 mmol 4,7-Diphenyl-2,9-dimethyl-1,10-phenanthroline (trade name: NEOCUPROINE) and 30 mmol N-bromosuccinimide are dissolved in carbon tetrachloride 150 ml. After the solution is refluxed for 30 minutes 30 mg. benzoyl peroxide is added to the solution, and then reflux is continued for 2 hours. The unreacted succinimide is removed from the reaction liquid by filtration. The resulting solution is dried to obtain 8 mmol 4,7-diphenyl-2,9-dibromomethyl-1,10-phenanthroline.

Thus obtained 2 mmol phenanthroline compound is dissolved in 500 ml of acetonitrile containing 5 mmol of ammonia and refluxed at about 100° C. for 18 hours. The reaction liquid is cooled to a room temperature, filtered and dried to obtain 2,2′,2″,9,9′,9″-bis[nitrilotri(-methylene)]tris(4,7-diphenyl-1,10-phenanthroline) in an amount of 6 mmol.

To a solution containing 40 ml trimethy orthoformate 10 ml in acetonitrile is added 0.4 mmol europium nitrate and refluxed for 1 hour in the atomosphere of nitrogen. To the solution is further added a solution of 0.4 mmol 2,2′,2″,9,9′,9″-bis[nitrilotri-(methylene)]tris(4,7-diphenyl-1,10-phenanthroline) in 10 ml of acetonitril and refluxed for 3 hours. After cooling to a room temperature, the reaction liquid is filtered and dried to obtain 0.25 mmol 2,2′,2″,9,9′,9″-bis[nitrilotri(methylene)]-tris(4,7-diphenyl-1,10-phenanthroline) europium.

To 2 ml of 97% pure chlorosulfonic acid is added 1.0 mmol of 2,2′,2″,9,9′,9″-bis[nitrilotri(methylene)]tris(4,7-diphenyl-1,10-phenanthroline) europium and the solution is stirred at 80° C. for 4 hours. The reaction liquid is cooled to a room temperature and filtered to obtain 0.95 mmol of 2,2′,2″,9,9′,9″-bis[nitrilotri-(methylene)]-tris(4,7-dichlorosulfonylphenyl-1,10-phenanthroline) europium.

EXAMPLE 2

2 mmol 2,2′,2″,9,9′,9″-bis[nitrilotri(methylene)]-tris(4,7-dichlorosulfonylphenyl-1,10-phenanthroline) europium obtained in Example 1 is dissolved in 0.5 ml of ethanol and added drop by drop slowly to a carbonate buffer solution (100 mmol, pH 9.2) containing 0.72 mol bovine serum albumin(BSA). The reaction liquid is subjected to an affinity chromatography using sephadex-5 column to obtain the labelled BSA which is excited by light of 337 nm and confirmed by the fluorescece at 613 nm based on europium ion, by means of a fluorescence photometer.

EXAMPLE 3

Example 1 is repeated to obtain 2,2′,2″,9,9′,9″-bis-[nitrilotri(methylene)]tris (1,10-phenanthroline) europium, provided that 2,9-dimethyl-1,0-phenanthroline is used in place of 4,7-diphenyl-2,9-dimethyl-1, 10-phenanthroline.

What is claimed is:

1. A protein labelled covalently with a lanthanide complex of europium cryptate of 2,2′,2″,9,9′,9″-bis[nitrilotri(methylene)]tris(1,10-phenanthroline) of the formula

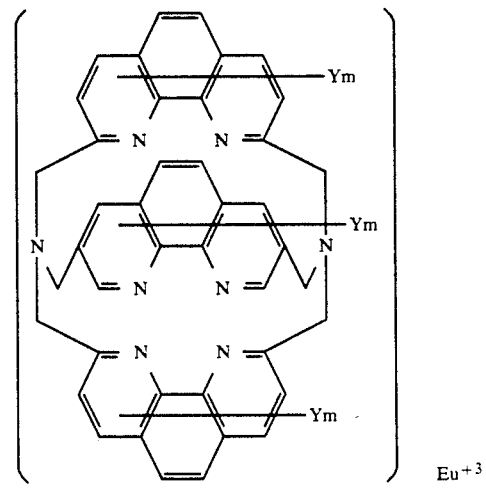

wherein Y is a halosulfonyl functional group or Y is a phenyl group containing a halosulfonyl functional group, and wherein the total number of m is at least 1 and each m is 0, 1 or 2, and wherein said protein is bovine serum albumin.

2. The protein according to claim 1, wherein the halosulfonyl functional group is chlorosulfonyl.

* * * * *